(12) United States Patent
Washburn

(10) Patent No.: US 6,555,519 B2
(45) Date of Patent: Apr. 29, 2003

(54) O-GLUCOSYLATED BENZAMIDE SGLT2 INHIBITORS AND METHOD

(75) Inventor: William N. Washburn, Titusville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 3 days.

(21) Appl. No.: 09/791,186

(22) Filed: Feb. 23, 2001

(65) Prior Publication Data

US 2002/0052326 A1 May 2, 2002

Related U.S. Application Data

(60) Provisional application No. 60/193,308, filed on Mar. 30, 2000.

(51) Int. Cl.[7] .................. A61K 31/35; A61K 31/135; A61K 31/155; A61K 31/175; A61K 31/335; A61K 38/28; C07H 17/02

(52) U.S. Cl. .................. 514/3; 514/449; 514/460; 514/593; 514/635; 514/652; 536/17.9

(58) Field of Search .................. 514/3, 449, 460, 514/593, 635, 652; 536/17.9

(56) References Cited

U.S. PATENT DOCUMENTS 5,444,050 A    8/1995    Kogan et al.

FOREIGN PATENT DOCUMENTS

| DE | 3632536 A | 7/1987 |
|---|---|---|
| EP | 0 598359 A1 | 5/1994 |
| EP | 0 684 254 B1 | 11/1995 |
| EP | 0 773 226 B1 | 5/1997 |
| EP | 0 850 948 A1 | 1/1998 |
| EP | 0 997472 A2 | 5/2000 |
| JP | 9124684 | 11/1995 |
| JP | 9124685 | 11/1995 |
| JP | 8-27006 | 1/1996 |
| JP | 9188625 | 11/1996 |
| JP | 10245391 | 3/1997 |
| WO | WO 97/01335 | 1/1997 |
| WO | WO 9831697 A | 7/1998 |
| WO | WO 0 018918 | 4/2000 |

OTHER PUBLICATIONS

Kosuge, T. et al, Chem. Pharm. Bull., vol. 24, 1976, p. 176–178.
T. Kuribayashi et al., Journal of Carbohydrate Chemistry, (1999) vol. 18, No. 4, pp. 371–382.
W. Gaffield et al., Tetrahedron, (1978) vol. 34, No. 20, pp. 3089–3096.
Benhaddou et al. Carbohydrate Research 260 (1994) pp. 243–250.
Hongu et al. Chemical Phar. Bull. (1998) vol. 46, No. 10, pp. 1545–1555.
Tsujihara et al. Chemical Pharm. Bull. (1996) vol. 44. No. 6. pp. 1174–1180.
Hongu et al. Chem. Pharm. Bull. (1998) vol. 46. No. 1, pp. 22–23.
Oku et al. Diabetes. vol. 48 (1999) pp. 1794–1800.

*Primary Examiner*—Raymond Henley, III
(74) *Attorney, Agent, or Firm*—John M. Kilcoyne; Jonathan N. Provoost

(57) ABSTRACT

SGLT2 inhibiting compounds are provided having the formula

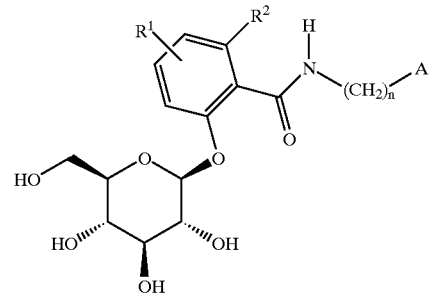

wherein
n is 0, 1 or 2;
A is

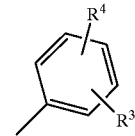

or heteroaryl which may contain 1 to 4 heteroatoms in the ring which may be selected from N, O, S, SO, and/or $SO_2$, bearing substituents $R^3$ and $R^4$;
and $R^1$ to $R^4$ are as defined herein.
A method is also provided for treating diabetes and related diseases employing an SGLT2 inhibiting amount of the above compound alone or in combination with one, two or more other antidiabetic agents and/or one, two or more hypolipidemic agents.

24 Claims, No Drawings

US 6,555,519 B2

O-GLUCOSYLATED BENZAMIDE SGLT2 INHIBITORS AND METHOD

This application takes priority from U.S. provisional application No. 60/193,308, filed Mar. 30, 2000.

FIELD OF THE INVENTION

The present invention relates to O-glucosylated benzamides which are inhibitors of sodium dependent glucose transporters found in the intestine and kidney (SGLT2) and to a method for treating diabetes, especially type II diabetes, as well as hyperglycemia, hyperinsulinemia, obesity, hypertriglyceridemia, Syndrome X, diabetic complicaitons, atherosclerosis and related diseases, employing such O-glucosylated benzamides alone or in combination with one, two or more other type antidiabetic agents and/or other type therapeutic agents such as hypolipidemic agents.

BACKGROUND OF THE INVENTION

Approximately 100 million people worldwide suffer from type II diabetes (NIDDM), which is characterized by hyperglycemia due to excessive hepatic glucose production and peripheral insulin resistance, the root causes for which are as yet unknown. Hyperglycemia is considered to be the major risk factor for the development of diabetic complications, and is likely to contribute directly to the impairment of insulin secretion seen in advanced NIDDM. Normalization of plasma glucose in NIDDM patients would be predicted to improve insulin action, and to offset the development of diabetic complications. An inhibitor of the sodium-dependent glucose transporter SGLT2 in the kidney would be expected to aid in the normalization of plasma glucose levels, and perhaps body weight, by enhancing glucose excretion.

The development of novel, safe, and orally active antidiabetic agents is also desired in order to complement existing therapies, including the sulfonylureas, thiazolidinediones, metformin, and insulin, and to avoid the potential side effects associated with the use of these other agents.

Hyperglycemia is a hallmark of type II diabetes (NIDDM); consistent control of plasma glucose levels in diabetes can offset the development of diabetic complications and beta cell failure seen in advanced disease. Plasma glucose is normally filtered in the kidney in the glomerulus and actively reabsorbed in the proximal tubule. SGLT2 appears to be the major transporter responsible for the reuptake of glucose at this site. The SGLT specific inhibitor phlorizin or closely related analogs inhibit this reuptake process in diabetic rodents and dogs resulting in normalization of plasma glucose levels by promoting glucose excretion without hypoglycemic side effects. Long term (6 month) treatment of Zucker diabetic rats with an SGLT2 inhibitor has been reported to improve insulin response to glycemia, improve insulin sensitivity, and delay the onset of nephropathy and neuropathy in these animals, with no detectable pathology in the kidney and no electrolyte imbalance in plasma. Selective inhibition of SGLT2 in diabetic patients would be expected to normalize plasma glucose by enhancing the excretion of glucose in the urine, thereby improving insulin sensitivity, and delaying the development of diabetic complications.

Ninety percent of glucose reuptake in the kidney occurs in the epithelial cells of the early S1 segment of the renal cortical proximal tubule, and SGLT2 is likely to be the major transporter responsible for this reuptake. SGLT2 is a 672 amino acid protein containing 14 membrane-spanning segments that is predominantly expressed in the early S1 segment of the renal proximal tubules. The substrate specificity, sodium dependence, and localization of SGLT2 are consistent with the properties of the high capacity, low affinity, sodium-dependent glucose transporter previously characterized in human cortical kidney proximal tubules. In addition, hybrid depletion studies implicate SGLT2 as the predominant $Na^+$/glucose cotransporter in the S1 segment of the proximal tubule, since virtually all Na-dependent glucose transport activity encoded in mRNA from rat kidney cortex is inhibited by an antisense oligonucleotide specific to rat SGLT2. SGLT2 is a candidate gene for some forms of familial glucosuria, a genetic abnormality in which renal glucose reabsorption is impaired to varying degrees. None of these syndromes investigated to date map to the SGLT2 locus on chromosome 16. However, the studies of highly homologous rodent SGLTs strongly implicate SGLT2 as the major renal sodium-dependent transporter of glucose and suggest that the glucosuria locus that has been mapped encodes an SGLT2 regulator. Inhibition of SGLT2 would be predicted to reduce plasma glucose levels via enhanced glucose excretion in diabetic patients.

SGLT1, another Na-dependent glucose cotransporter that is 60% identical to SGLT2 at the amino acid level, is expressed in the small intestine and in the more distal S3 segment of the renal proximal tubule. Despite their sequence similarities, human SGLT1 and SGLT2 are biochemically distinguishable. For SGLT1, the molar ratio of $Na^+$ to glucose transported is 2:1, whereas for SGLT2, the ratio is 1:1. The Km for $Na^+$ is 32 and 250–300 mM for SGLT1 and SGLT2, respectively. $K_m$ values for uptake of glucose and the nonmetabolizable glucose analog α-methyl-D-glucopyranoside (AMG) are similar for SGLT1 and SGLT2, i.e. 0.8 and 1.6 mM (glucose) and 0.4 and 1.6 mM (AMG) for SGLT1 and SGLT2 transporters, respectively. However, the two transporters do vary in their substrate specificities for sugars such as galactose, which is a substrate for SGLT1 only.

Administration of phlorizin, a specific inhibitor of SGLT activity, provided proof of concept in vivo by promoting glucose excretion, lowering fasting and fed plasma glucose, and promoting glucose utilization without hypoglycemic side effects in several diabetic rodent models and in one canine diabetes model. No adverse effects on plasma ion balance, renal function or renal morphology have been observed as a consequence of phlorizin treatment for as long as two weeks. In addition, no hypoglycemic or other adverse effects have been observed when phlorizin is administered to normal animals, despite the presence of glycosuria. Administration of an inhibitor of renal SGLTs for a 6-month period (Tanabe Seiyaku) was reported to improve fasting and fed plasma glucose, improve insulin secretion and utilization in obese NIDDM rat models, and offset the development of nephropathy and neuropathy in the absence of hypoglycemic or renal side effects.

Phlorizin itself is unattractive as an oral drug since it is a nonspecific SGLT1/SGLT2 inhibitor that is hydrolyzed in the gut to its aglycone phloretin, which is a potent inhibitor of facilitated glucose transport. Concurrent inhibition of facilitative glucose transporters (GLUTs) is undesirable since such inhibitors would be predicted to exacerbate peripheral insulin resistance as well as promote hypoglycemia in the CNS. Inhibition of SGLT1 could also have serious adverse consequences as is illustrated by the hereditary syndrome glucose/galactose malabsorption (GGM), in which mutations in the SGLT1 cotransporter result in impaired glucose uptake in the intestine, and life-threatening diarrhea and dehydration. The biochemical differences between SGLT2 and SGLT1, as well as the degree of sequence divergence between them, allow for identification of selective SGLT2 inhibitors.

The familial glycosuria syndromes are conditions in which intestinal glucose transport, and renal transport of other ions and amino acids, are normal. Familial glycosuria patients appear to develop normally, have normal plasma glucose levels, and appear to suffer no major health deficits as a consequence of their disorder, despite sometimes quite high (110–114 g/daily) levels of glucose excreted. The major symptoms evident in these patients include polyphagia, polyuria and polydipsia, and the kidneys appear to be normal in structure and function. Thus, from the evidence available thus far, defects in renal reuptake of glucose appear to have minimal long term negative consequences in otherwise normal individuals.

The following references disclose O-aryl glucosides SGLT2 inhibitors for treating diabetes.

EP 598359A1 (also JP 035988) (Tanabe Seiyaku) discloses compounds of the following structure A

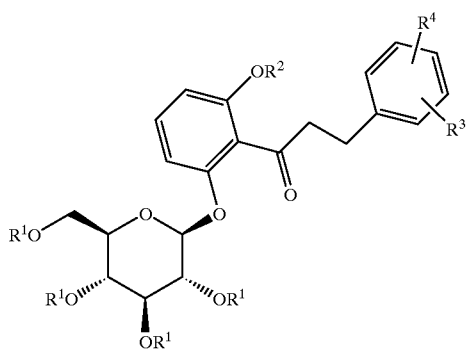

$R^1$ = H, acyl,
$R^2$ = H, Me
$R^4$, $R^4$ can be a variety of substituents

EP 0850948A1 discloses the following structures of genus B

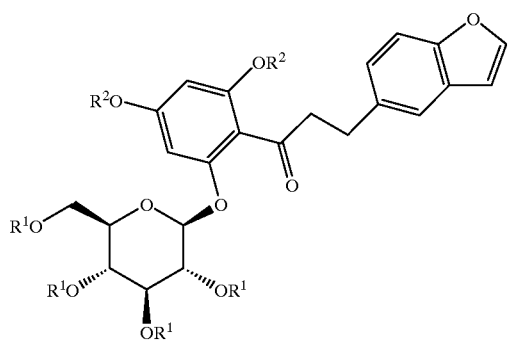

$R^1$ = H, acyl, CO(OAlkyl)
$R^2$ = H, allyl
$R^3$ = H or Me

JP 09188625A expands upon structure B to include examples of B where $R^3$ is H and where the 5 membered ring is saturated as well as the counterparts of benzothiophenes (O=S) and indenes (O=CH$_2$). EP 684254-A1 appears to encompass derivatives of structure B disclosed in JP 09188625A.

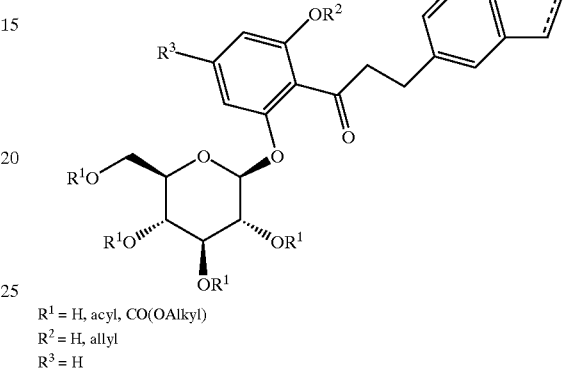

$R^1$ = H, acyl, CO(OAlkyl)
$R^2$ = H, allyl
$R^3$ = H

JP 09124685A expands upon structure B for $R^3$=H to include derivatives of mono acylated C6 hydroxyl where the acyl group is a substituted benzoic or pyridyl carboxylic acid or a urethane generated from the corresponding phenol.

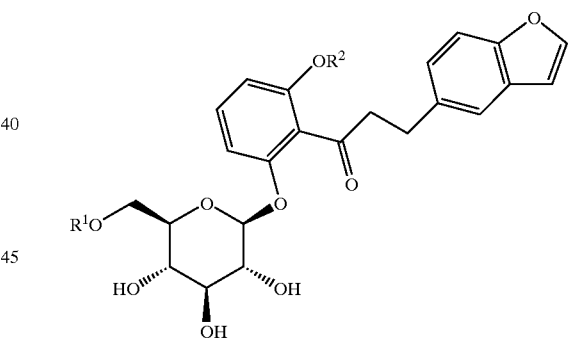

$R^1$ = H, CO-aryl, CO(OAryl)
$R^2$ = H

JP 09124684 discloses derivatives of structure B

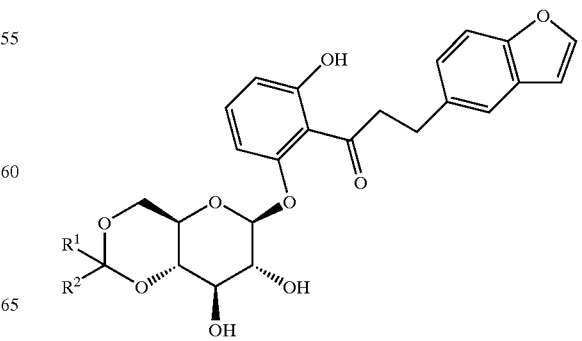

$R^1$, $R^2$ = H, alkyl, alkoxy, aryl or together oxo)

EP 773226-A1 discloses derivatives of structure B

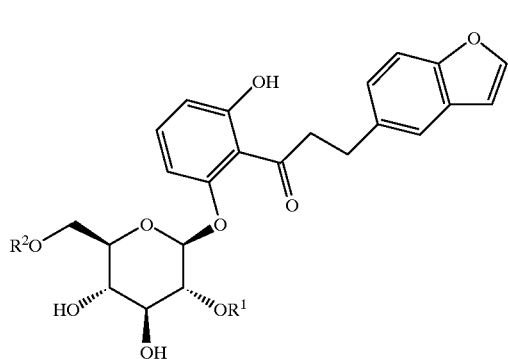

$R^1$ = alkanoyl if $R^2$ = H
$R^2$ = alkoxycarbonyl if $R^1$ = H

EP 850948-A1 discloses the following alkylated derivatives of Structure B

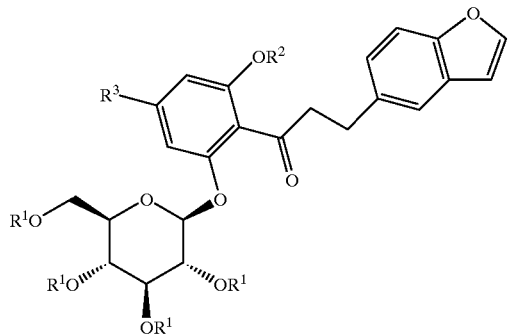

$R^1$ = H, acyl, CO(OAlkyl)
$R^2$ = H, allyl
$R^3$ = Lower alkyl

JP 08027006-A discloses derivatives of structure A where various combinations of the glucose hydroxyl are acylated and appears to be similar to EP 598359A1.

Other disclosures and publications which disclose SGLT2 inhibitors are as follows:

K. Tsujihara, et. al., Chem. *Pharm. Bull.* 44, 1174–1180 (1996)

M. Hongu et. al., Chem. *Pharm. Bull.* 46, 22–33 (1998)

M. Hongu et. al., Chem. *Pharm. Bull.* 46, 1545–1555 (1998)

A. Oku et. al., *Diabetes,* 48, 1794–1800 (1999)

JP 10245391 (Dainippon) discloses 500 structures as hypoglycemic agents for treatment of diabetes. These are O-glucosides of hydroxylated coumarins.

Other references disclosing structures of O-aryl glucosides, shown below, which are closely related to the genus disclosed herein are:

N. Shinma et. al., EP 51819 A2 which discloses structures of the following genus

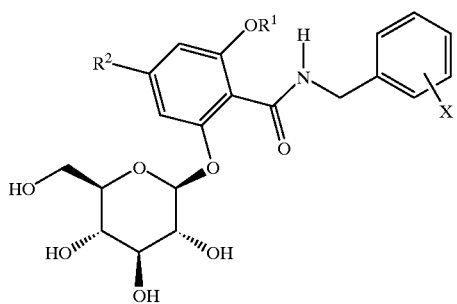

$R^1$ = alkyl
$R^2$ = alkoxy, S-alkyl, O-alkenyl
X = hydrogen or substituent

DESCRIPTION OF THE INVENTION

In accordance with the present invention, O-glucosylated benzamide compounds are provided which have the structure

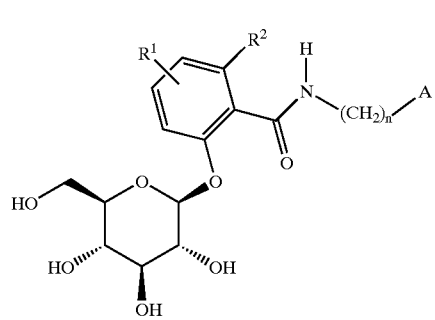

I.

wherein
n is 0, 1 or 2;
A is

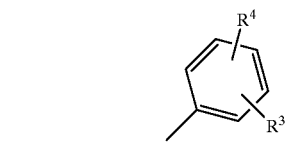

or heteroaryl which may contain 1 to 4 heteroatoms in the ring which may be selected from N, O, S, SO, and/or $SO_2$, bearing substituents $R^3$ and $R^4$;

$R^1$ is selected from hydrogen, $OR^5$, lower alkyl, aryl, arylalkyl, $NHCOR^5$, $NR^6R^{6a}$, or halogen;

$R^2$ is selected from hydrogen, OH, $OR^{5a}$, or lower alkyl;

$R^3$ and $R^4$ are the same or different and are independently selected from hydrogen, OH, $OR^{5b}$, OAryl, $OCH_2$Aryl, lower alkyl, cycloalkyl, aryl, arylalkyl, $CF_3$, —$SCF_3$, —$OCHF_2$, —$OCF_3$, halogen, —CN, —$CO_2R^{5c}$, —$CO_2H$, —$CONR^{6b}$ $R^{6c}$, —$NR^{6d}R^{6e}$, —$SO_2NH_2$, —$NHCOR^{5d}$, —$NHSO_2R^{5e}$—$NHSO_2$Aryl,—$SR^{5f}$,—$SOR^{5g}$,—$SO_2R^{5h}$, —$SO_2$ Aryl, —$OCH_2CO_2R^{5i}$, —$OCH_2CO_2H$, —$OCH_2CONR^{6f}R^{6g}$, —$OCH_2CH_2NR^{6h}R^{6i}$, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5, R^{5a}, R^{5b}, R^{5c}, R^{5d}, R^{5e}, R^{5f}, R^{5g}, R^{5h}$, and $R^{5i}$ are independently lower alkyl;

$R^6, R^{6a}, R^{6b}, R^{6c}, R^{6d}, R^{6e}, R^{6f}, R^{6g}, R^{6h}$, and $R^{6i}$ are the same or different and are independently selected from hydrogen, alkyl, aryl, arylalkyl or cycloalkyl;

and a pharmaceutically acceptable salt thereof, all stereoisomers thereof, and all prodrug esters thereof.

The compounds of formula I of the invention as defined above also include the following proviso that where A is

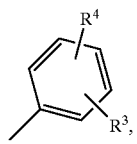

and n=1, when $R^2$ is alkoxy, $R^1$ cannot be alkoxy.

The compounds of formula I of the invention possess activity as inhibitors of the sodium dependent glucose transporters found in the intestine and kidney of mammals and are useful in the treatment of diabetes and the micro- and macro-vascular complications of diabetes such as retinopathy, neuropathy, nephropathy, and wound healing.

The present invention provides for compounds of formula I, pharmaceutical compositions employing such compounds and for methods of using such compounds.

In addition, in accordance with the present invention, a method is provided for treating diabetes, especially type II diabetes, and related diseases including complications of diabetes, including retinopathy, neuropathy, nephropathy and wound healing, and related diseases such as insulin resistance, hyperglycemia, hyperinsulinemia, Syndrome X, elevated blood levels of fatty acids or glycerol, obesity, hypertriglyceridemia, atherosclerosis and hypertension, and for increasing high density lipoprotein levels, wherein a therapeutically effective amount of a compound of structure I of the invention is administered to a human patient in need of treatment.

In addition, in accordance with the present invention, a method is provided for treating diabetes and related diseases as defined above and hereinafter, wherein a therapeutically effective amount of a combination of a compound of structure I of the invention and one, two or more other types antidiabetic agents and/or one, two or more other types of therapeutic agents is administered to a human patient in need of treatment.

The conditions, diseases, and maladies collectively referred to as "Syndrome X" (also known as Metabolic Syndrome) are detailed in Johannsson J. *Clin. Endocrinol. Metabl.*, 82, 727–34 (1997).

The term "other types of therapeutic agents" as employed herein refers to one or more antidiabetic agents (other than SGLT2 inhibitors of formula I), one or more anti-obesity agents, and/or one or more lipid-lowering agents (including anti-atherosclerosis agents).

In the above method of the invention, the compound of structure I will be employed in a weight ratio to the antidiabetic agent(s) and/or other types of therapeutic agent (s) (depending upon its mode of operation) within the range from about 0.01:1 to about 300:1, preferably from about 0.1:1 to about 100:1, and more preferably from about 0.1:1 to about 10:1.

Preferred are compounds of formula IA of structure IA

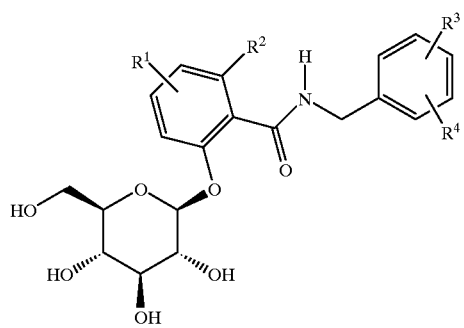

wherein $R^1$ is hydrogen.

More preferred are compounds of formula IA where $R^1$ and $R^3$ are each H;

$R^2$ is hydrogen or OH;

$R^4$ is a para substituent.

Most preferred are compounds of formula I of the structure IB

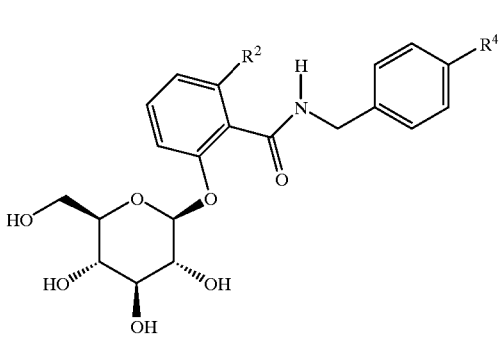

where $R^2$ is hydrogen or OH;

$R^4$ is alkyl, $R^{5b}O$, $CHF_2$, $CF_3O$ or $R^{5f}S$.

Examples of preferred compounds of formula I of the invention include

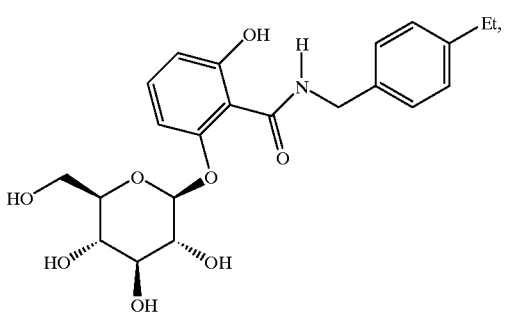

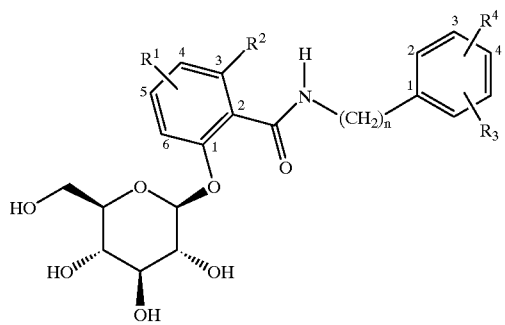

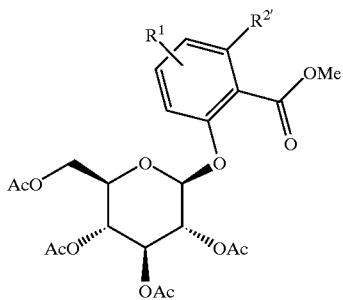

| $R^1$ and $R^3$ | $R^2$ | n | $R^4$ | MS or LC/MS $(M + H)^+$ |
|---|---|---|---|---|
| H | HO | 1 | 4-MeO | 436 |
| H | HO | 1 | 4-Me | 420 |
| H | HO | 1 | 4-CHF$_2$O | 472 |
| H | HO | 1 | 4-n-Pr | 448 |
| H | HO | 1 | 4-n-Pentyl | 476 |

DETAILED DESCRIPTION OF THE INVENTION

The present invention provides for compounds of formula I, pharmaceutical compositions employing such compounds and for methods of using such compounds.

The compounds of formula I of the invention may be prepared as shown in the following reaction schemes and description thereof wherein temperatures are expressed in degrees Centigrade.

Compounds of formula I of the invention can be prepared according to Scheme 1 by coupling compounds of formula II

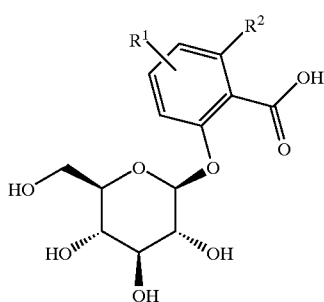

with compounds of formula III

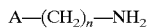

Compounds of formula III are either commercially available or can be prepared by one skilled in the art.

Compounds of formula II are prepared from compounds of formula IV,

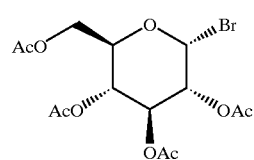

where $R^{2'}$ is selected from hydrogen, acetoxy, alkoxy, and alkyl, by treatment with a base such as LiOH or NaOH in a solvent such as 3:1 MeOH/H$_2$O or 3:2:1 MeOH/THF/H$_2$O.

Compounds of formula IV can be prepared by coupling commercially available 2,3,4,6-tetra-O-acetyl-α-D-glucopyranosyl bromide V

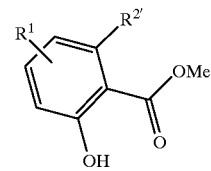

with compounds of formula VI

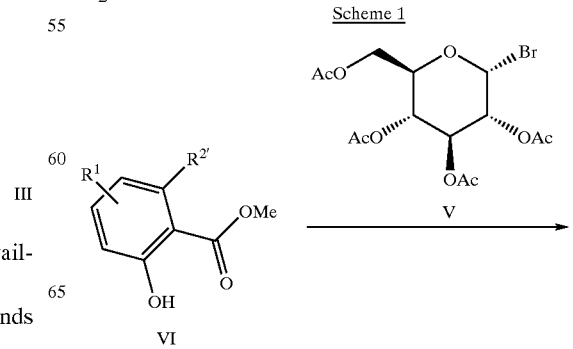

in the presence of Ag$_2$O in a solvent such as lutidine or quinoline or in the presence of silver triflate in a solvent such as CH$_2$Cl$_2$ containing a base such as 2,6 di-t-butyl-4-methylpyridine.

Many compounds of formula VI are commercially available. However, compounds of formula VI, where $R^{2'}$ is acetoxy, can be prepared by sequential treatment of 2,6-dihydroxybenzoic acid with Ac$_2$O containing a strong acid such as H$_2$SO$_4$, then with TMSCHN$_2$ in a solvent such as 20% MeOH/PhMe, and finally with catalytic amounts of a base such as LiOH in solvent such as 3:2:1 MeOH/THF/H$_2$O.

Scheme 1

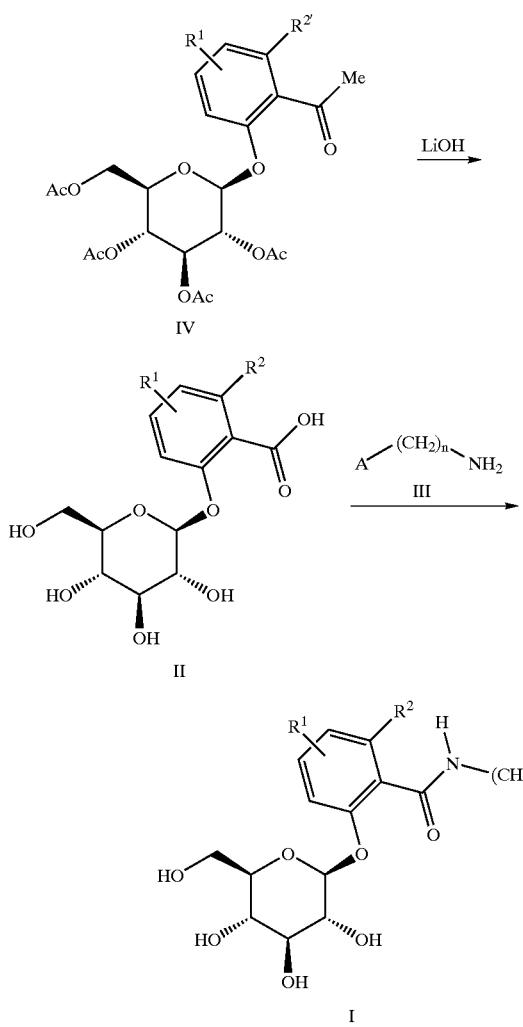

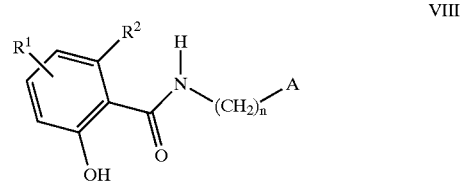

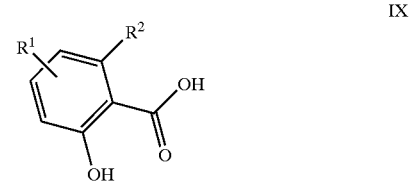

in the presence of $Ag_2O$ in a solvent such as lutidine or quinoline or in the presence of silver triflate in a solvent such as $CH_2Cl_2$ containing a base such as 2,6 di-t-butyl-4-methylpyridine.

Compounds of formula VIII can be prepared by coupling amines of formula III with acids of formula IX employing standard procedures known to those skilled in the art.

Scheme 2

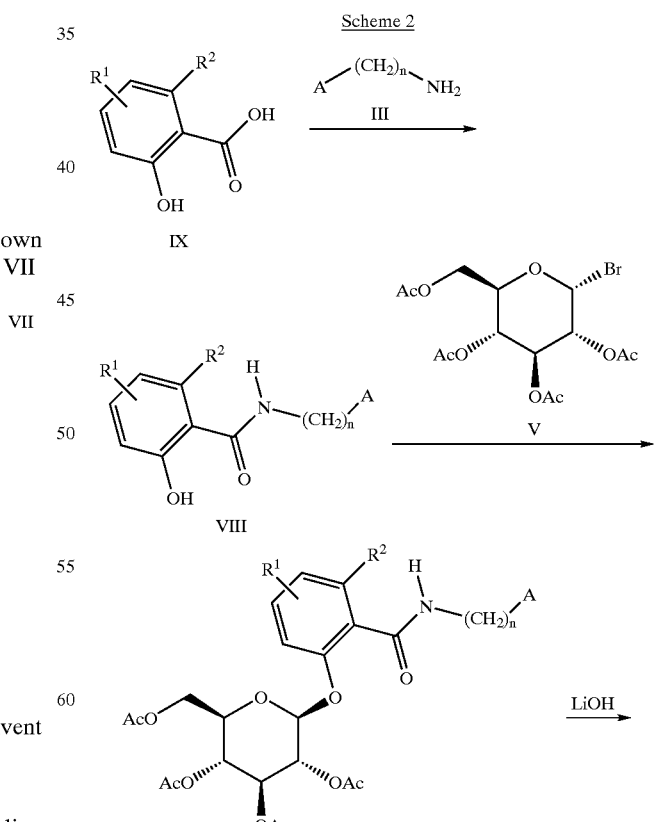

Compounds of formula I can also be prepared (as shown in Scheme 2) by hydrolysis of compounds of formula VII

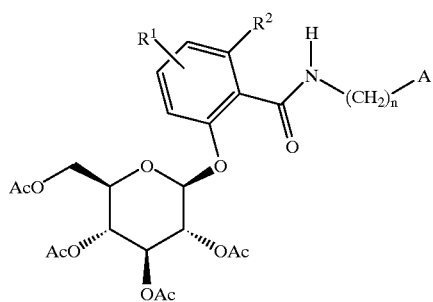

by treatment with a base such as LiOH or NaOH in a solvent such as 3:1 $MeOH/H_2O$ or 3:2:1 $MeOH/THF/H_2O$.

Compounds of formula VII can be prepared by coupling commercially available 2,3,4,6-tetra-O-acetyl-α-D-glucopyranosyl bromide V with amides of formula VIII -continued

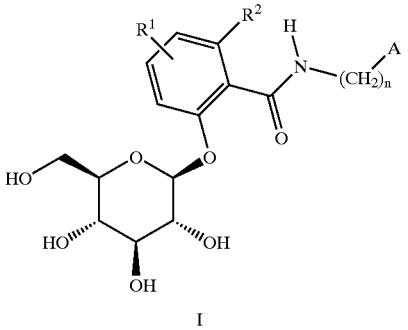

I

Listed below are definitions of various terms used to describe the compounds of the instant invention.

These definitions apply to the terms as they are used throughout the specification (unless they are otherwise limited in specific instances) either individually or as part of a larger group.

The following abbreviations are employed herein:
Ph=phenyl
Bn=benzyl
t-Bu=tertiary butyl
Me=methyl
Et=ethyl
TMS=trimethylsilyl
$TMSN_3$=trimethylsilyl azide
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3$N=triethylamine
DMAP=4-dimethylaminopyridine
$NaBH_4$=sodium borohydride
$LiAlH_4$=lithium aluminum hydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
HOBT or HOBT.$H_2$O=1-hydroxybenzotriazole hydrate
HOAT=1-Hydroxy-7-azabenzotriazole
$Ph_3$P=triphenylphosphine
Pd(OAc)$_2$=Palladium acetate
$(Ph_3P)_4Pd^0$=tetrakis triphenylphosphine palladium
Ar=argon
$N_2$=nitrogen
min=minute(s)
h or hr=hour(s)
L=liter
mL=milliliter
$\mu$=microliter
g=gram(s)

mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point
dppf=diphenylphosphinoferrocene
DCE=1,2-dichloroethane Unless otherwise indicated, the term "lower alkyl", "alky" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, optionally substituted amino, hydroxy, hydroxyalkyl, acyl, oxo, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl, any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the alkyl substituents.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12- tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylakyl", "arylalkenyl" and "arylalkynyl" as used alone or as part of another group refer to alkyl, alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_n$ or $(CH_2)_p$ (where p is 1 to 8, preferably 1 to 5, which includes alkylene, alkenylene or alkynylene groups as defined herein), may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy.

Examples of $(CH_2)_n$ or $(CH_2)_p$, alkylene, alkenylene and alkynylene include —$CH_2$—, —$CH_2CH_2$—,

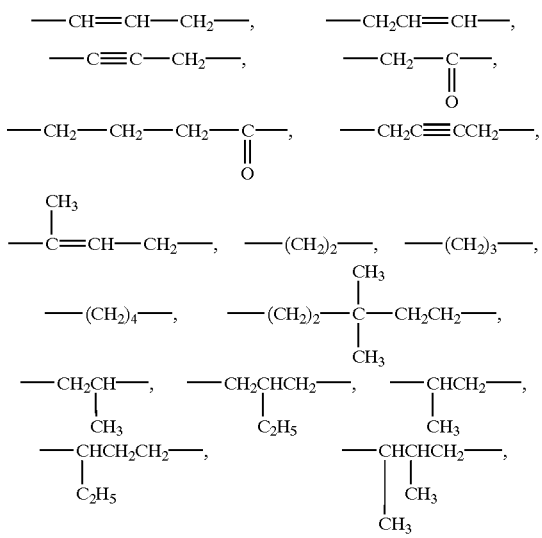

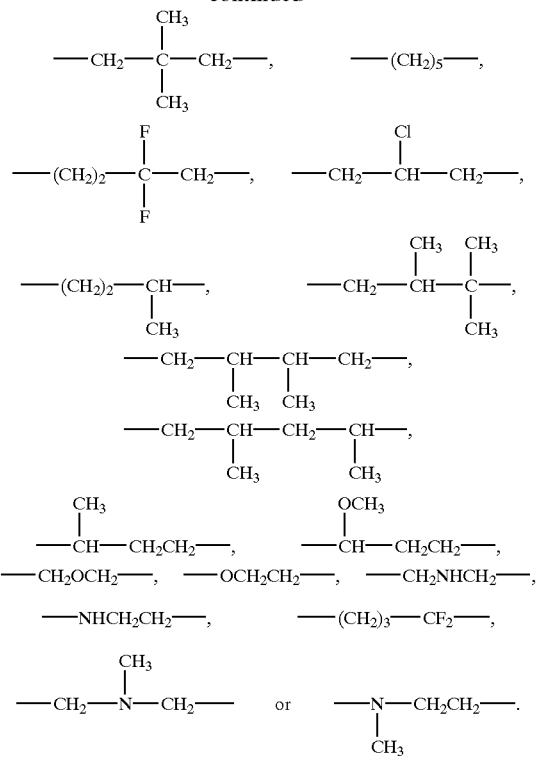

The term "halogen" or "halo" as used herein alone or as part of another group refers to chlorine, bromine, fluorine, and iodine, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" or "Aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

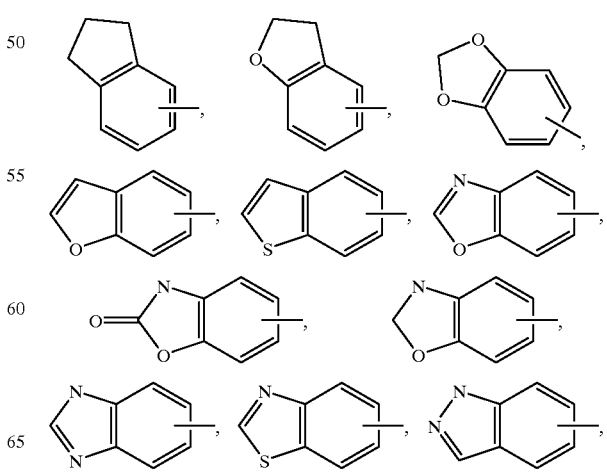

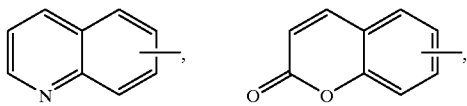

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the alkyl substituents as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the alkyl substituents attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (where p is 1, 2 or 3), such as

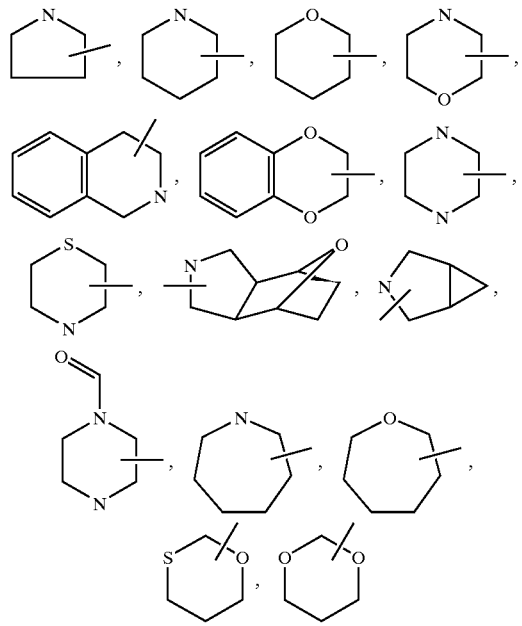

and the like. The above groups may include 1 to 4 substituents such as alkyl, halo, oxo and/or any of of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur,and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the the alkyl substituents set out above. Examples of heteroaryl groups include the following:

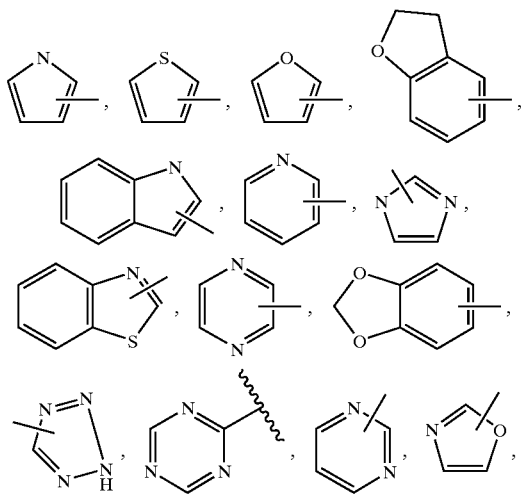

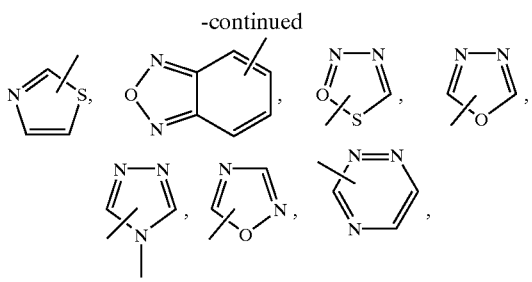

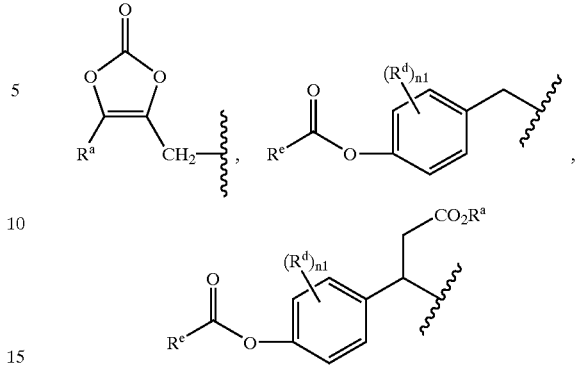

and the like.

The term "cycloheteroalkylalkyl" as used herein alone or as part of another group refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "five, six or seven membered carbocycle or heterocycle" as employed herein refers to cycloalkyl or cycloalkenyl groups as defined above or heteroaryl groups or cycloheteroaryl groups as defined above, such as thiadiazaole, tetrazole, imidazole, or oxazole.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like. In addition, prodrug esters which are known in the art for carboxylic and phosphorus acid esters such as methyl, ethyl, benzyl and the like.

Examples of such prodrug esters include

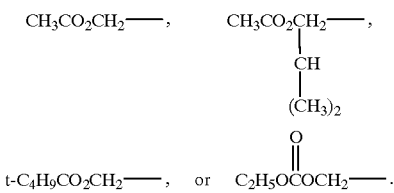

Other examples of suitable prodrug esters include

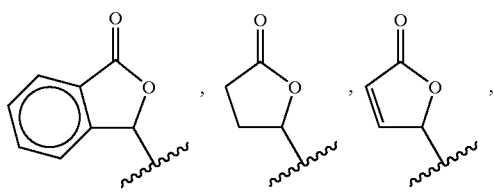

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

Where the compounds of structure I are in acid form they may form a pharmaceutically acceptable salt such as alkali metal salts such as lithium, sodium or potassium, alkaline earth metal salts such as calcium or magnesium as well as zinc or aluminum and other cations such as ammonium, choline, diethanolamine, lysine (D or L), ethylenediamine, t-butylamine, t-octylamine, tris-(hydroxymethyl) aminomethane (TRIS), N-methyl glucosamine (NMG), triethanolamine and dehydroabietylamine.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more other types of antidiabetic agents and/or one or more other types of therapeutic agents which may be administered orally in the same dosage form, in a separate oral dosage form or by injection.

The other type of antidiabetic agent which may be optionally employed in combination with the SGLT2 inhibitor of formula I may be 1,2,3 or more antidiabetic agents or antihyperglycemic agents including insulin secretagogues or insulin sensitizers, or other antidiabetic agents preferably having a mechanism of action different from SGLT2 inhibition and may include biguanides, sulfonyl ureas, glucosidase inhibitors, PPAR γ agonists, such as thiazolidinediones, aP2 inhibitors, PPAR α/γ dual agonists, dipeptidyl peptidase IV (DP4) inhibitors, and/or meglitinides, as well as insulin, and/or glucagon-like peptide-1 (GLP-1).

It is believed that the use of the compounds of structure I in combination with 1, 2, 3 or more other antidiabetic agents produces antihyperglycemic results greater than that possible from each of these medicaments alone and greater than the combined additive anti-hyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compounds of structure I will be employed in a weight ratio to biguanide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.5:1 to about 50:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulino®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer), isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.2:1 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1(7–36) amide, GLP-1(7–37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. provisional application No. 60/155,400, filed Sep. 22, 1999, (attorney file LA29) the disclosure of which is incorporated herein by reference, employing dosages as set out therein, which compounds designated as preferred are preferred for use herein.

The other antidiabetic agent may be an aP2 inhibitor such as disclosed in U.S. application Ser. No. 09/391,053, filed Sep. 7, 1999, and in U.S. provisional application No. 60/127, 745, filed Apr. 5, 1999 (attorney file LA27*), employing dosages as set out herein. Preferred are the compounds designated as preferred in the above application.

The other antidiabetic agent may be a DP4 inhibitor such as disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl) amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The SGLT2 inhibitor of formula I will be employed in a weight ratio to the meglitinide, PPAR γ agonist, PPAR α/γ dual agonist, aP2 inhibitor or DP4 inhibitor within the range from about 0.01:1 to about 100:1, preferably from about 0.2:1 to about 10:1.

The hypolipidemic agent or lipid-lowering agent which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712, 279, and 5,760,246.

The most preferred MTP inhibitor is 9-[4-[4-[[2-(2,2,2-Trifluoroethoxy)benzoyl]amino]-1-piperidinyl] butyl]-N-(2, 2,2-trifluoroethyl)-9H-fluorene-9-carboxamide

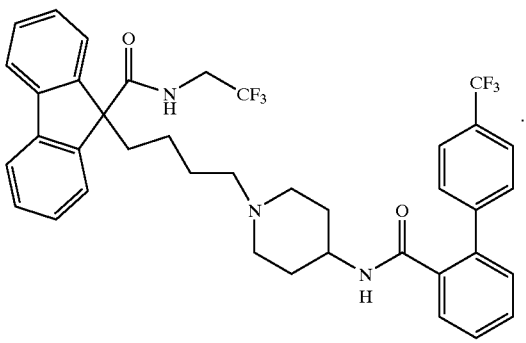

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. No. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin, cerivastatin, atavastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians'Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The other type of therapeutic agent which may be optionally employed with the SGLT2 inhibitor of formula I may be 1, 2, 3 or more of an anti-obesity agent including a beta 3 adrenergic agonist, a lipase inhibitor, a serotonin (and dopamine) reuptake inhibitor, a thyroid receptor beta drug and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO99/00353 (KaroBio) and GB98/284425 (KaroBio), with compounds of the KaroBio applications being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

In carrying our the method of the invention for treating diabetes and related diseases, a pharmaceutical composition will be employed containing the compounds of structure I, with or without other antidiabetic agent(s) and/or antihyperlipidemic agent(s) and/or other type therapeutic agents, in association with a pharmaceutical vehicle or diluent. The pharmaceutical composition can be formulated employing conventional solid or liquid vehicles or diluents and pharmaceutical additives of a type appropriate to the mode of desired administration such as pharmaceutically acceptable carriers, excipients, binder and the like. The compounds can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid dosage forms will contain from about 10 to about 500 mg of a compound of formula I. The dose for adults is preferably between 10 and 2,000 mg per day, which can be administered in a single dose or in the form of individual doses from 1–4 times per day.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

SGLT2 inhibitor activity of the compounds of the invention may be determined by use of an assay system as set out below.

Assay for SGLT2 Activity

The mRNA sequence for human SGLT2 (GenBank #M95549) was cloned by reverse-transcription and amplification from human kidney mRNA, using standard molecular biology techniques. The cDNA sequence was stably transfected into CHO cells, and clones were assayed for SGLT2 activity essentially as described in Ryan et al. (1994). Evaluation of inhibition of SGLT2 activity in a clonally selected cell line was performed essentially as described in Ryan et al., with the following modifications.

Cells were grown in 96-well plates for 2–4 days to 75,000 or 30,000 cells per well in F-12 nutrient mixture (Ham's F-12), 10% fetal bovine serum, 300 μg/ml Geneticin and penicillin-streptomycin. At confluence, cells were washed twice with 10 mM Hepes/Tris, pH 7.4, 137 mM N-methyl-D-glucamine, 5.4 mM KCl, 2.8 mM $CaCl_2$, 1.2 mM $MgSO_4$. Cells then were incubated with 10 μM [$^{14}$C] AMG, and 10 μM inhibitor (final DMSO =0.5%) in 10 mM Hepes/Tris, pH 7.4, 137 mM NaCl, 5.4 mM KCl, 2.8 mM $CaCl_2$, 1.2 mM $MgSO_4$ at 37° C. for 1.5 hr. Uptake assays were quenched with ice cold 1× PBS containing 0.5 mM phlorizin, and cells were then lysed with 0.1% NaOH. After addition of MicroScint scintillation fluid, the cells were allowed to shake for 1 hour, and then [$^{14}$C] AMG was quantitated on a TopCount scintillation counter. Controls were performed with and without NaCl. For determination of $EC_{50}$ values, 10 inhibitor concentrations were used over 2 log intervals in the appropriate response range, and triplicate plates were averaged across plates. Ryan M J, Johnson G, Kirk J, Fuerstenberg S M, Zager R A and Torok-Storb B. 1994. HK-2: an immortalized proximal tubule epithelial cell line from normal adult human kidney. Kidney International 45: 48–57.

The following Working Examples represent preferred embodiments of the present invention. All temperatures are expressed in degrees Centigrade unless otherwise indicated.

EXAMPLE 1

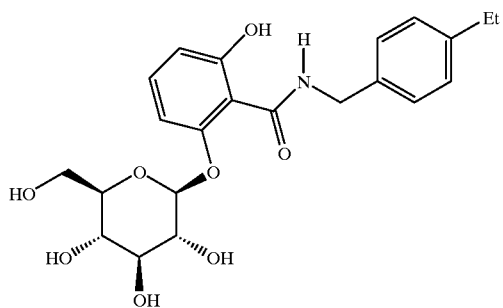

A. 4-Ethylbenzylamine

A mixture of 4-ethylbenzoic acid (0.50 g, 3.33 mmol) in $SOCl_2$ (1 mL) and DMF(1 drop) was refluxed for 2 h. The reaction mixture was concentrated and then stripped with toluene (2×10 mL) to yield 4-ethylbenzoyl chloride (0.59 g, >100%) as a colorless oil. The crude acid chloride (0.59 g, 3.5 mmol) in toluene (minimum amount) was added dropwise to conc. aq. $NH_4OH$ (1.4 mL). After stirring for 1 h, the reaction mixture was concentrated, the residue was dissolved in water and extracted with EtOAc (3×25 mL). The combined organic layers were washed with 1 N aq. NaOH (10 mL) and brine and dried over $Na_2SO_4$ prior to removal of the volatiles to yield 4-ethylbenzamide (460 mg, 88%) as a white solid. A suspension of this crude amide (430 mg, 2.87 mmol) and $LiAlH_4$ (180 mg, 4.7 mmol) in dry THF (5 mL) was refluxed at 65° C. for 4.5 h. More $LiAlH_4$ (60 mg, 1.58 mmol) was added, and the reaction mixture was heated at 65° C. for 2 h. The reaction mixture was cooled, and 1 N aq. NaOH (0.4 mL) was added. After stirring for 4 h, the mixture was filtered, and the filtrate was concentrated to give 4-ethylbenzylamine (350 mg, 90w) as a pale yellow oil.

B. 2,6-Diacetoxybenzoic Acid

A solution of 2,6-dihydroxybenzoic acid (4.72 g, 30 mmol) in $Ac_2O$ (16 g, 14.2 mL) containing 5 drops of conc. $H_2SO_4$ was heated with stirring at 80° for 2 hr until tlc analysis indicated the reaction was complete. The solution was poured onto ice/$H_2O$ and extracted 3× with EtOAc. The combined organic phases were washed 4× with $H_2O$ and once with brine prior to drying over $Na_2SO_4$. After removal of the volatiles using a rotary evaporator, 5.8 g of 2,6-diacetoxybenzoic acid was obtained as a white solid which was used without further purification.

C. Methyl 2,6-diacetoxybenzoate

To a stirred 4° solution of Part B 2,6-diacetoxybenzoic acid (5.8 g, mmol) in 4:1 PhMe/MeOH (25 mL) was added 17 mL of 2M $TMSCHN_2$/hexane over 10 min. After tlc analysis (1:1 ETOAc/hexane) revealed complete conversion, the volatiles were removed using a rotary evaporator and the residue purified by silica gel chromatography. 1:1 $CH_2Cl_2$/hexane-$CH_2Cl_2$ eluted 4.5 g of methyl 2,6-diacetoxybenzoate.

D. Methyl 2-acetoxy-6-hydroxybenzoate

A solution of Part C methyl 2,6-diacetoxybenzoate (3.4 g, 14 mmol) and $LiOH.H_2O$ (60 mg, 1.5 mmol) in 2:2:1 MeOH/THF/$H_2O$ (30 mL) was stirred for 2 hr at 20° until tlc analysis (4:1 hexane/EtOAc) revealed comparable amounts of starting bis-acetate and methyl 2,6-dihydroxybenzoate. The solution was quenched with pH 7 $Na_2HPO_4$ buffer, diluted with $H_2O$ prior to 4 EtOAc extractions. The combined organic phase was washed with $H_2O$ 2×, brine 1× prior to drying over $Na_2SO_4$. After removal of the volatiles, chromatography on silica gel using 3:2 hexane/$CH_2Cl_2$ eluted 1.1 g of a 1:2 mixture of methyl 2,6-dihydroxybenzoate/methyl 2-acetoxy-6-hydroxybenzoate followed by 0.7 g of pure methyl 2-acetoxy-6-hydroxybenzoate. Re-chromatography of the mixed fraction yielded another 0.8 g of methyl 2-acetoxy-6-hydroxybenzoate.

E

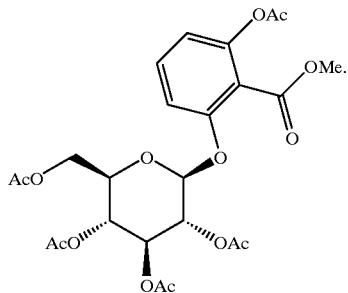

To a stirred 5° C. suspension of Part D methyl 2-acetoxy-6-hydroxybenzoate (1.0 g, 4.8 mmol) and $Ag_2O$ (0.57 g, 2.4 mmol) in quinoline (5 mL) was added 2,3,4, 6-tetra-O-acetyl-α-D-glucopyranosyl bromide (Aldrich) (1.8 g, 4.5 mmol). After the reaction mixture became thick, more quinoline (1.5 mL) was added, and stirring was continued for 3 h. The reaction mixture was diluted with $CH_2Cl_2$ and filtered through a pad of Celite® washing with $CH_2Cl_2$. The filtrate was washed with 1 N HCl (5×), water (1×), sat'd aq. $NaHCO_3$ (2×) and brine prior to drying over $Na_2SO_4$, and the mixture was filtered. After concentrating the filtrate, the residue was purified by silica gel column chromatography. 2:1 Hexane/EtOAc eluted the free phenol counterpart of the title compound (0.35 g, 15%); 1:1 hexane:ethyl acetate eluted the desired tetra-acetoxy glucoside (1.3 g, 50%).

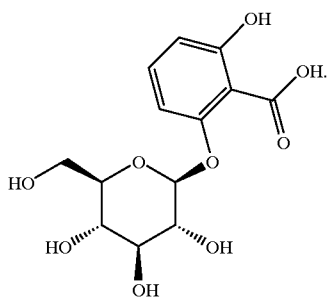

F

A solution of Part E glucoside (2.1 g, 3.89 mmol) in 1:2:2 H₂O/THF/MeOH (25 mL) was treated with LiOH.H₂O (1.26 g, 30 mmol). After stirring overnight at ambient temperature, 1 N HCl (25 mL) was added until the pH was ~3. The reaction mixture was stripped several times with MeOH until dry. The residue was dissolved in 10% MeOH in water and purified by prep HPLC in two injections using a YMC C₁₈ column (S-10 ODS 30×500 mm) eluting at 28 ml/min with 11% MeOH/H₂O containing 0.1% TFA. The combined product fractions were concentrated and lyophilized to afford title 0-glucosylated benzoic acid (1.14 g, 93%) as a white lyophilate.

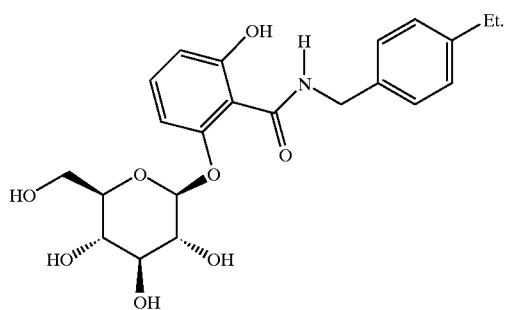

G

To a solution of Part F O-glucosylated benzoic acid (40 mg, 0.120 mmol) in dry DMF (1 mL) was added 4-ethylbenzylamine (20.5 mg, 0.152 mmol) followed by HOAT (18.9 mg, 0.139 mmol) and EDCC (25.4 mg, 0.133 mmol). After stirring overnight at ambient temperature, the reaction mixture was diluted with EtOAc and washed with H₂O (3×10 mL). The combined aqueous layers were extracted with EtOAc. The combined organic layers were washed with brine and dried over MgSO₄. The mixture was filtered; the filtrate was concentrated to give an oily residue. The residue, after dissolving in 7:3 MeOH/H₂O (~2 mL), was purified by prep HPLC (column: YMC S5 ODS 20×100 mm) eluting with a gradient system of 40% to 90% MeOH/H₂O to give the final product (27 mg, 49%) as a white solid after concentration and lyophilization.

¹H-NMR (400 MHz, CD3-OD): δ 7.30–7.28 (m, 3H), 7.167 (d, 2H), 6.87 (d, 1H), 6.61 (d, 1H), 4.98 (d, 1H), 4.54 (ABq, 2H), 3.89 (dd, 1H), 3.67 (dd, 1H), 3.45–3.30 (m, 3H), 2.61 (q, 2H), 1.21 (t, 3H)

LRMS Calculated for C21H26O6 (M+H+): 434, Found: 434

HPLC YMC S5 ODS 4.6×50 mm Ballistic, 8 minute gradient, 2.5 ml/min, 3 minute hold, retention time =6.56 min.

EXAMPLE 1 VIA METHOD 2

An alternative procedure for the preparation of Example 1 from 2,6-dihydroxybenzoic acid and 4-ethylbenzylamine is summarized below:

A. N-(4-ethylbenzyl)-2,6-dihydroxybenzamide

Following the procedure described in Example 1 Part G above, N-(4-ethylbenzyl)-2,6-dihydroxybenzamide was prepared from 2,6-dihydroxybenzoic acid (276 mg, 1.8 mmol) and 4-ethylbenzylamine (290 mg, 2.15 mmol). Purification by silica gel column chromatography, eluting with 1:6 EtOAc/hexanes gave the desired amide (293 mg, 60%) as a white solid.

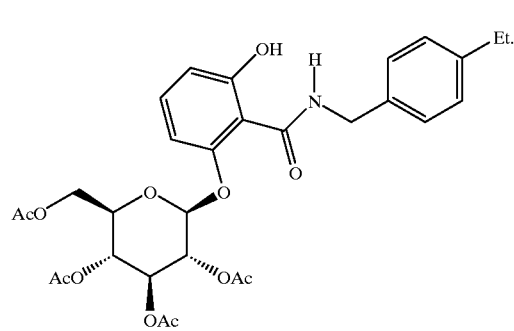

B

To a suspension of Part A N-(4-ethylbenzyl)-2,6-dihydroxybenzamide (275 mg, 1.01 mmol) and Ag₂O (468 mg, 2.02 mmol) in 2,6-lutidine (2–3 mL) was added 2,3,4,6-tetra-O-acetyl-α-D-glucopyranosyl bromide (0.5 g, 1.22 mmol). After stirring overnight at ambient temperature, the reaction mixture was diluted with CH₂Cl₂ (~20 mL) and filtered through a pad of Celite® 545, washing with CH₂Cl₂. The filtrate was concentrated, then stripped with PhMe (4×10 mL) to remove 2,6-lutidine to yield a dark brown syrup (0.721 g). Purification by silica gel column chromatography, eluting with 1:2 EtOAc/hexanes, gave the tetra acetate (331 mg, 55%) as a white solid.

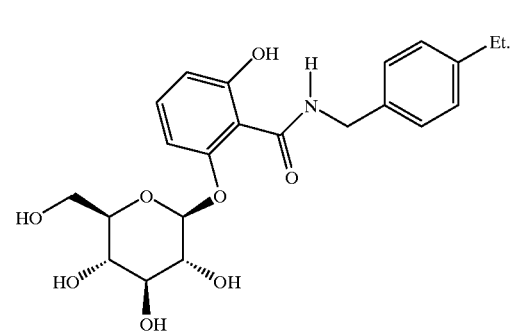

C

A solution of Part B tetra acetate (150 mg, 0.25 mmol) and LiOH.H₂O (52 mg, 1.25 mmol) in 1:2:3 H₂O/THF/MeOH (5 mL) was stirred for 2 h at ambient temperature. After removal of the volatiles, the residue was dissolved in ~1:2 MeOH/H₂O (4 mL) and purified by prep HPLC in two injections on a C18 column (YMC S5 ODS 20×100 mm), by gradient elution with 40% to 90% MeOH/H₂O over 20 min to afford the title compound (96 mg, 89%) as a white solid after concentration and lyophilization

EXAMPLES 2 TO 56

In a manner analogous to that of Example 1, the benzamides in the following table were prepared. Preparative HPLC purification of the benzamides varied slightly in regards to column and the eluting solvent gradient. Many of the precursor amines were commercially available; non-commercially available amines were prepared in an analogous manner to that summarized in Part A.

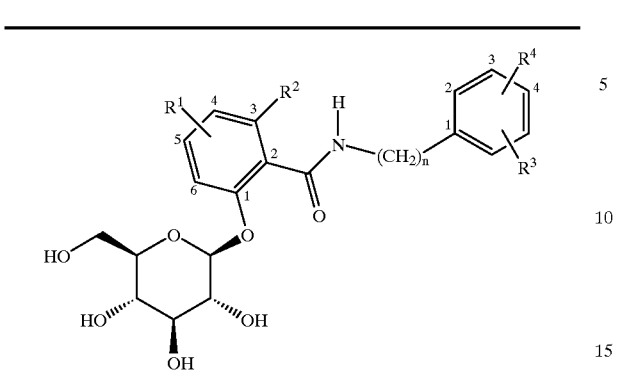

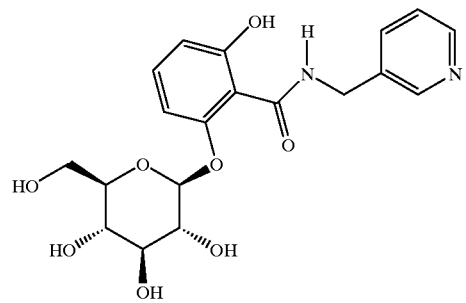

Example 53
M + H 407

| Ex. # | R¹ | R² | n | R⁴ (R³ = H)[a] | MS or LC/MS (M + H)⁺ |
|---|---|---|---|---|---|
| 2 | H | HO | 1 | H | 406 |
| 3 | H | HO | 1 | 4-MeO | 436 |
| 4 | H | HO | 1 | 4-Thiadiazyl | 490 |
| 5 | H | HO | 1 | 4-Me | 420 |
| 6 | H | HO | 1 | 4-Cl | 440 |
| 7 | H | HO | 1 | 4-CF₃ | 474 |
| 8 | H | HO | 1 | 4-NMe₂ | 449 |
| 9 | H | HO | 1 | 4-SO₂NH₂ | 485 |
| 10 | H | HO | 1 | 4-t-Bu | 462 |
| 11 | H | HO | 1 | 4-CF₃O | 490 |
| 12 | H | HO | 1 | 4-Ph | 482 |
| 13 | H | HO | 1 | 4-SEt | 466 |
| 14 | H | HO | 1 | 4-CHF₂O | 472 |
| 15 | H | HO | 1 | 4-i-Pr | 448 |
| 16 | H | HO | 1 | 4-n-Pr | 448 |
| 17 | H | HO | 1 | 4-n-Pentyl | 476 |
| 18 | H | HO | 1 | 4-n-Bu | 462 |
| 19 | H | HO | 1 | 4-n-PrO | 464 |
| 20 | H | HO | 1 | 4-CF₃S | 506 |
| 21 | H | HO | 1 | 4-EtO | 450 |
| 22 | H | HO | 1 | 3-MeO | 436 |
| 23 | H | HO | 1 | 3-CF₃ | 474 |
| 24 | H | HO | 1 | 3-Me | 420 |
| 25 | H | HO | 1 | 3-Cl | 440 |
| 26 | H | HO | 1 | 2-MeO | 436 |
| 27 | H | HO | 1 | 3,4-(MeO)₂ | 466 |
| 28 | H | HO | 1 | 3,4-(Cl)₂ | 474 |
| 29 | H | HO | 1 | 3,4-OCH₂O | 450 |
| 30 | 4-(p-MeOBn) | HO | 1 | 4-MeO | 556 |
| 31 | H | H | 1 | 4-MeO | 420 |
| 32 | H | H | 1 | 4-CF₃ | 458 |
| 33 | H | H | 1 | 4-CF₃O | 474 |
| 34 | H | MeO | 1 | 4-MeO | 450 |
| 35 | H | Ph | 1 | 4-MeO | 496 |
| 36 | H | Me | 1 | 4-MeO | 434 |
| 37 | H | i-Pr | 1 | 4-MeO | 462 |
| 38 | 4-Me | H | 1 | 4-MeO | 434 |
| 39 | 4-Cl | H | 1 | 4-MeO | 454 |
| 40 | 4-MeO | H | 1 | 4-MeO | 450 |
| 41 | 4-AcNH | H | 1 | 4-MeO | 477 |
| 42 | 4-Me₂N | H | 1 | 4-MeO | 463 |
| 43 | 5-Me | H | 1 | 4-MeO | 434 |
| 44 | 5-Cl | H | 1 | 4-MeO | 454 |
| 45 | 5-MeO | H | 1 | 4-MeO | 450 |
| 46 | 5-F | H | 1 | 4-MeO | 438 |
| 47 | 5-Br | H | 1 | 4-MeO | 498 |
| 48 | H | MeO | 1 | 4-MeO | 450 |
| 49 | H | HO | 0 | 4-MeO | 422 |
| 50 | H | H | 0 | H | 376 |
| 51 | H | HO | 2 | H | 420 |
| 52 | H | HO | 2 | 3,4-(MeO)₂ | 480 |

[a]Unless otherwise indicated

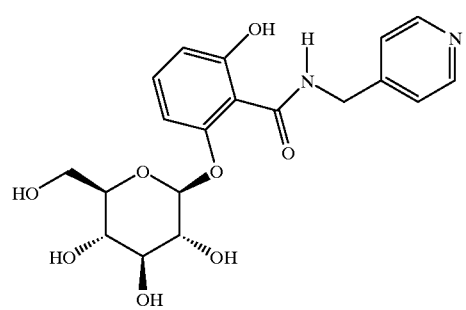

Example 54
M + H 407

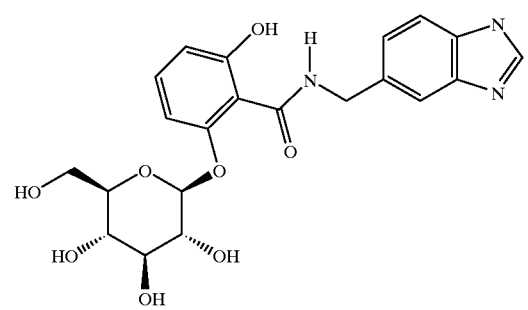

Example 55
M + H 445

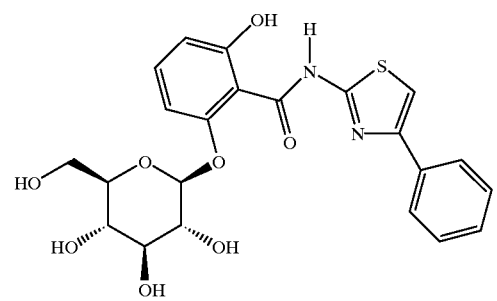

Example 56
M + H 475

What is claimed:

1. A compound having the structure

[Chemical structure showing a benzamide with glucose/sugar moiety, substituents R¹, R², and N-(CH₂)ₙ-A]

wherein n is 0, 1 or 2;

A is

[Chemical structure of aryl group with R³ and R⁴ substituents]

or heteroaryl which may contain 1 to 4 heteroatoms in the ring which may be selected from N, O, S, SO, and/or $SO_2$, bearing substituents $R^3$ and $R^4$;

$R^1$ is selected from hydrogen, $OR^5$, lower alkyl, aryl, arylalkyl, $NHCOR^5$, $NR^6R^{6a}$, or halogen;

$R^2$ is selected from hydrogen, OH, $OR^{5a}$, or lower alkyl;

$R^3$ and $R^4$ are the same or different and are independently selected from hydrogen, OH, $OR^{5b}$, OAryl, $OCH_2Aryl$, lower alkyl, cycloalkyl, aryl, arylalkyl, $CF_3$, $-SCF_3$, $-OCHF_2$, $-OCF_3$, halogen, $-CN$, $-CO_2R^{5c}$, $-CO_2H$, $-CONR^{5b}R^{5c}$, $-NR^{5d}R^{5e}$, $-SO_2NH_2$, $-NHCOR^{5d}$, $-NHSO_2R^{5e}$, $-NHSO_2Aryl$, $-SR^{5f}$, $-SOR^{5g}$, $-SO_2R^{5h}$, $-SO_2Aryl$, $-OCH_2CO_2R^{5i}$, $-OCH_2CO_2H$, $-OCH_2CONR^{6f}R^{6g}$, $-OCH_2CH_2NR^{6h}R^{6i}$, or a five, six or seven membered heterocycle which may contain 1 to 4 heteroatoms in the ring which are N, O, S, SO, and/or $SO_2$, or $R^3$ and $R^4$ together with the carbons to which they are attached form an annelated five, six or seven membered carbocycle or heterocycle which may contain 1 to 4 heteroatoms in the ring which are N, O, S, SO, and/or $SO_2$;

$R^5$, $R^{5a}$, $R^{5b}$, $R^{5c}$, $R^{5d}$, $R^{5e}$, $R^{5f}$, $R^{5g}$, $R^{5h}$, and $R^{5i}$ are independently lower alkyl; $R^6$, $R^{6a}$, $R^{6b}$, $R^{6c}$, $R^{6d}$, $R^{6e}$, $R^{6f}$, $R^{6g}$, $R^{6h}$, and $R^{6i}$ are the same or different and are independently selected from hydrogen, alkyl, aryl, arylalkyl or cycloalkyl;

and a pharmaceutically acceptable salt thereof, all stereoisomers thereof, and all prodrug esters thereof, with the proviso that where A is

[Chemical structure of aryl group with R³ and R⁴ substituents]

and n=1, when $R^2$ is alkoxy, $R^1$ cannot be alkoxy.

2. The compound as defined in claim 1 wherein A is

[Chemical structure of aryl group with R³ and R⁴ substituents]

3. The compound as defined in claim 1 wherein A is heteroaryl.

4. The compound as defined in claim 1 wherein $R^1$ is H.

5. The compound as defined in claim 2 wherein $R^1$ and $R^3$ are each H, and $R^2$ is OH or H.

6. The compound as defined in claim 1 wherein n is 1.

7. The compound as defined in claim 1 having the structure

[Chemical structure showing benzamide with glucose moiety and benzyl group]

wherein $R^1$ is H.

8. The compound as defined in claim 7 wherein $R^1$ and $R^3$ are each H, and $R^2$ is H or OH, and $R^4$ is in the para-position.

9. The compound as defined in claim 1 having the structure

[Chemical structure showing benzamide with glucose moiety and para-substituted benzyl group]

where $R^2$ is hydrogen or OH; and $R^4$ is alkyl, $R^{5b}O$, $CHF_2O$, $CF_3O$ or $R^{5f}S$.

10. The compound as defined in claim 1 having the structure

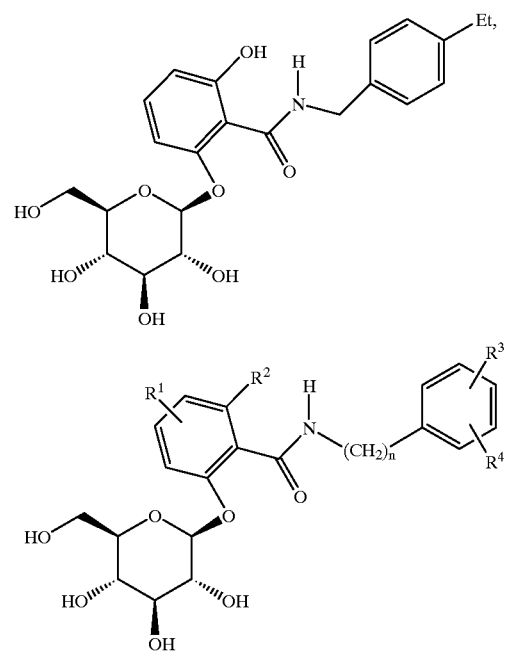

| R¹ | R² | n | R⁴ (R³ = H)ᵃ | MS or LC/MS (M + H)⁺ |
|---|---|---|---|---|
| H | HO | 1 | H | 406 |
| H | HO | 1 | 4-MeO | 436 |
| H | HO | 1 | 4-Thiadiazyl | 490 |
| H | HO | 1 | 4-Me | 420 |
| H | HO | 1 | 4-Cl | 440 |
| H | HO | 1 | 4-CF₃ | 474 |
| H | HO | 1 | 4-NMe₂ | 449 |
| H | HO | 1 | 4-SO₂NH₂ | 485 |
| H | HO | 1 | 4-t-Bu | 462 |
| H | HO | 1 | 4-CF₃O | 490 |
| H | HO | 1 | 4-Ph | 482 |
| H | HO | 1 | 4-SEt | 466 |
| H | HO | 1 | 4-CHF₂O | 472 |
| H | HO | 1 | 4-i-Pr | 448 |
| H | HO | 1 | 4-n-Pr | 448 |
| H | HO | 1 | 4-n-Pentyl | 476 |
| H | HO | 1 | 4-n-Bu | 462 |
| H | HO | 1 | 4-n-PrO | 464 |
| H | HO | 1 | 4-CF₃S | 506 |
| H | HO | 1 | 4-EtO | 450 |
| H | HO | 1 | 3-MeO | 436 |
| H | HO | 1 | 3-CF₃ | 474 |
| H | HO | 1 | 3-Me | 420 |
| H | HO | 1 | 3-Cl | 440 |
| H | HO | 1 | 2-MeO | 436 |
| H | HO | 1 | 3,4-(MeO)₂ | 466 |
| H | HO | 1 | 3,4-(Cl)₂ | 474 |
| H | HO | 1 | 3,4-OCH₂O | 450 |
| 4-(p-MeOBn) | HO | 1 | 4-MeO | 556 |
| H | H | 1 | 4-MeO | 420 |
| H | H | 1 | 4-CF₃ | 458 |
| H | H | 1 | 4-CF₃O | 474 |
| H | MeO | 1 | 4-MeO | 450 |
| H | Ph | 1 | 4-MeO | 496 |
| H | Me | 1 | 4-MeO | 434 |
| H | i-Pr | 1 | 4-MeO | 462 |
| 4-Me | H | 1 | 4-MeO | 434 |
| 4-Cl | H | 1 | 4-MeO | 454 |
| 4-MeO | H | 1 | 4-MeO | 450 |
| 4-AcNH | H | 1 | 4-MeO | 477 |
| 4-Me₂N | H | 1 | 4-MeO | 463 |
| 5-Me | H | 1 | 4-MeO | 434 |
| 5-Cl | H | 1 | 4-MeO | 454 |
| 5-MeO | H | 1 | 4-MeO | 450 |
| 5-F | H | 1 | 4-MeO | 438 |
| 5-Br | H | 1 | 4-MeO | 498 |
| H | MeO | 1 | 4-MeO | 450 |
| H | HO | 0 | 4-MeO | 422 |
| H | H | 0 | H | 376 |
| H | HO | 2 | H | 420 |
| H | HO | 2 | 3,4-(MeO)₂ | 480 |

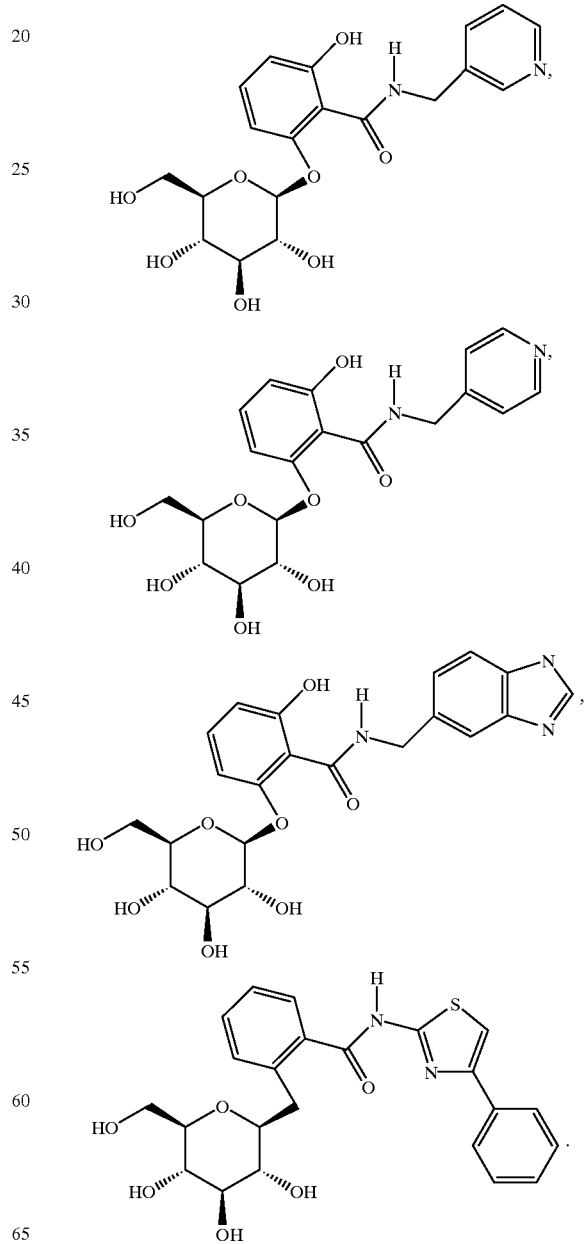

11. The compound as defined in claim 1 having the structure

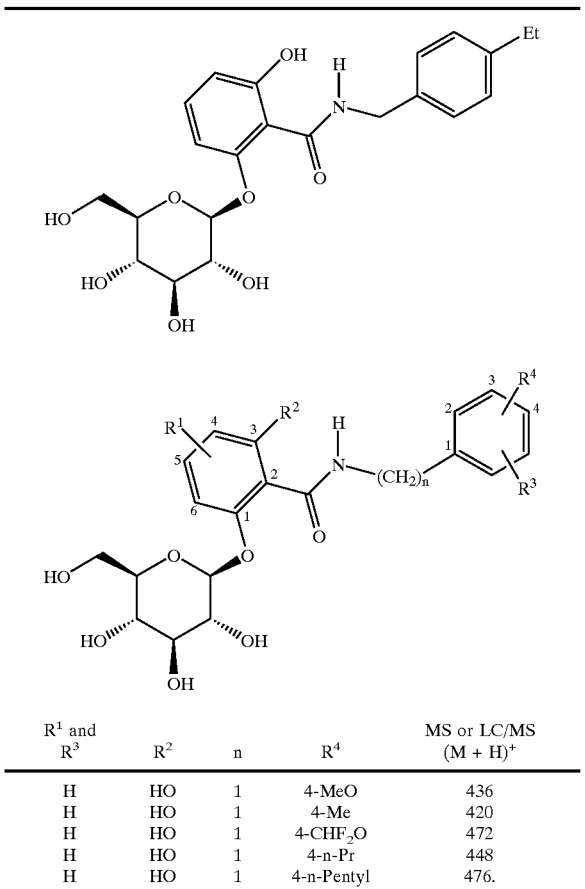

| $R^1$ and $R^3$ | $R^2$ | n | $R^4$ | MS or LC/MS $(M + H)^+$ |
|---|---|---|---|---|
| H | HO | 1 | 4-MeO | 436 |
| H | HO | 1 | 4-Me | 420 |
| H | HO | 1 | 4-CHF$_2$O | 472 |
| H | HO | 1 | 4-n-Pr | 448 |
| H | HO | 1 | 4-n-Pentyl | 476. |

12. A pharmaceutical composition comprising a compound as defined in claim 1 and a pharmaceutically acceptable carrier therefor.

13. A pharmaceutical combination comprising an SGLT2 inhibitor compound as defined in claim 1 and an antidiabetic agent other than an SGLT2 inhibitor, an anti-obesity agent and/or a lipid-lowering agent.

14. The pharmaceutical combination as defined in claim 13 comprising said SGLT2 inhibitor compound and an antidiabetic agent.

15. The combination as defined in claim 14 wherein the antidiabetic agent is 1, 2, 3 or more of a biguanide, a sulfonyl urea, a glucosidase inhibitor, a PPAR γ agonist, a PPAR α/γ dual agonist, an aP2 inhibitor, a DP4 inhibitor, an insulin sensitizer, a glucagon-like peptide-1 (GLP-1), insulin and/or a meglitinide.

16. The combination as defined in claim 15 wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, Gl-262570, isaglitazone, JTT-501, NN-2344, L895645, YM-440, R-119702, AJ9677, repaglinide, nateglinide, KAD1129, AR-HO39242, GW-409544, KRP297, AC2993, LY315902, and/or NVP-DPP-728A.

17. The combination as defined in claim 14 wherein the compound is present in a weight ratio to the antidiabetic agent within the range from about 0.01 to about 100:1.

18. The combination as defined in claim 13 wherein the anti-obesity agent is a beta 3 adrenergic agonist, a lipase inhibitor, a serotonin (and dopamine) reuptake inhibitor, a thyroid receptor beta compound, and/or an anorectic agent.

19. The combination as defined in claim 18 wherein the anti-obesity agent is orlistat, ATL-962, AJ9677, L750355, CP331648, sibutramine, topiramate, axokine, dexamphetamine, phentermine, phenylpropanolamine, and/or mazindol.

20. The combination as defined in claim 13 wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor.

21. The combination as defined in claim 20 wherein the lipid lowering agent is pravastatin, lovastatin, simvastatin, atorvastatin, cerivastatin, fluvastatin, nisvastatin, visastatin, fenofibrate, gemfibrozil, clofibrate, avasimibe, TS-962, MD-700, and/or LY295427.

22. The combination as defined in claim 20 wherein the SGLT2 inhibitor is present in a weight ratio to the lipid-lowering agent within the range from about 0.01 to about 300:1.

23. A method for treating diabetes, diabetic retinopathy, diabetic neuropathy, diabetic nephropathy, wound healing, insulin resistance, hyperglycemia, hyperinsulinemia, Syndrome X, diabetic complications, or elevated blood levels of free fatty acids or glycerol, hyperlipidemia, obesity, hypertriglyceridemia, atherosclerosis, hypertension, or for increasing high density lipoprotein levels, which comprises administering to a mammalian species in need of treatment a therapeutically effective amount of a compound as defined in claim 1.

24. A method for treating type II diabetes which comprises administering to a mammalian species in need of treatment a therapeutically effective amount of a compound as defined in claim 1 alone or in combination with one, two or more other antidiabetic agent(s) and/or one, two or more hypolipidemic agent(s).

* * * * *